United States Patent
Amano et al.

(10) Patent No.: US 6,447,652 B1
(45) Date of Patent: Sep. 10, 2002

(54) THIN-FILM FORMING METHOD AND THIN-FILM FORMING APPARATUS

(75) Inventors: Shunji Amano, Saitama; Hiroshi Hayashi, Kanagawa; Ryoichi Hiratsuka, Miyagi, all of (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/463,004

(22) PCT Filed: May 14, 1999

(86) PCT No.: PCT/JP99/02535

§ 371 (c)(1), (2), (4) Date: Apr. 5, 2000

(87) PCT Pub. No.: WO99/58740

PCT Pub. Date: Nov. 18, 1999

(30) Foreign Application Priority Data

May 14, 1998 (JP) .............................................. 10-132149

(51) Int. Cl.$^7$ .............................................. C23C 14/34
(52) U.S. Cl. .............................. 204/192.13; 204/192.11; 204/192.12; 204/192.16; 204/298.03; 204/298.04; 204/298.05; 204/298.24; 118/712; 118/723 R; 427/8; 427/527; 427/585
(58) Field of Search ...................... 204/192.13, 192.11, 204/192.12, 192.16, 298.04, 298.24, 298.05, 298.03; 427/8, 523, 585; 118/712, 723 R

(56) References Cited

U.S. PATENT DOCUMENTS 4,863,576 A * 9/1989 Collins et al. ......... 204/192.15
5,837,357 A * 11/1998 Matsuo et al. ............... 428/212

FOREIGN PATENT DOCUMENTS

| JP | 56-65974 | 6/1981 | ........... C23C/11/00 |
|----|----------|--------|------------------------|
| JP | 59-140524 | 8/1984 | .......... G05D/23/20 |
| JP | 61-194335 | 8/1986 | .......... G01N/21/65 |
| JP | 62-121322 | 6/1987 | ............. G01J/3/10 |
| JP | 04-270943 | 9/1992 | .......... G01N/21/27 |
| JP | 05-97581 | 4/1993 | ........... C30B/29/04 |
| JP | 05-102267 | 4/1993 | ........... H01L/21/66 |
| JP | 05-234917 | 9/1993 | ......... H01L/21/205 |
| JP | 05-332934 | 12/1993 | .......... G01N/21/65 |
| JP | 10-49856 | 2/1998 | ............. G11B/5/66 |

* cited by examiner

Primary Examiner—Steven H. VerSteeg
(74) Attorney, Agent, or Firm—Sonnenschein, Nath & Rosenthal

(57) ABSTRACT

A Raman spectrum of a thin film which must be formed is measured in a thin-film forming step for forming the thin film on a member to be processed in an atmosphere, the pressure of which has been reduced. Moreover, the conditions under which the thin film is formed are controlled in accordance with a result of measurement of the Raman spectrum. At this time, the measurement of the Raman spectrum is continuously performed in an in-line manner while the thin film is being continuously formed on the elongated-sheet-like member to be processed. The measurement of the Raman spectrum is performed while the focal point of a probe of a Raman spectrometer is being controlled with respect to the member to be processed or while the output of a laser beam from the Raman spectrometer is being controlled. The thin film which must be. formed is, for example, a protective film of a magnetic recording medium. The protective film is, for example, a hard carbon film (a DLC film).

21 Claims, 16 Drawing Sheets

THIN-FILM FORMING METHOD AND THIN-FILM FORMING APPARATUS

BACKGROUND OF THE INVENTION

1. Field of the Invention

The present invention relates to a thin-film forming method and a thin-film forming apparatus, and more particularly to a thin-film forming method and a thin-film forming apparatus capable of forming a thin film while evaluating the film characteristics by measuring a Raman spectrum.

2. Description of the Related Art

In recent years, the thin-film forming technique has progressed considerably resulting in a variety of modifications of the thin-film forming apparatus and the thin-film forming method of obtaining a thin film. In particular, a thin-film forming apparatus and a thin-film forming method arranged to employ a new technique for evaluating the thin film have been investigated. An exemplary thin film, a magnetic film and a protective film for use to constitute a magnetic recording medium are described below.

Magnetic recording mediums for magnetic disc apparatuses and those for digital video tape recorders have mainly been magnetic recording mediums, such as magnetic discs or evaporated tapes each incorporating a thin magnetic metal film. The structure of the magnetic recording medium may be described with reference to FIG. 1, which is a schematic cross sectional view showing the structure of the magnetic recording medium.

In general, a magnetic recording medium 101 is, as shown in FIG. 1, structured such that a non-magnetic support member 102 constituted by a polyethylene terephthalate film is formed. A magnetic film 103 constituted by a Fe—Co alloy film or the like is formed on the non-magnetic support member 102. Moreover, a protective film 104, such as a carbon film, is formed on the magnetic film 103. In recent years the magnetic film 103 has been protected from damage occurring due to head crush or the magnetic tape has been given wear resistance against sliding with respect to a magnetic head by providing a hard carbon film, that is, a so-called a diamond-like carbon film (hereinafter called a "DLC film").

One of the methods of evaluating the characteristics of the protective film 104, (such as the DLC film) specifically, a method of estimating the molecular structure and the composition ratio of the protective film 104, employs a Raman spectrum method. The foregoing method can estimate whether or not the crystal structure approximates the diamond structure.

An example of an analysis of the film characteristic by the foregoing Raman spectrum method is described with reference to FIG. 2, which shows an example of a typical Raman spectrometer.

The Raman spectrum method is structured such that a laser beam emitted from a laser-beam oscillator 111 is introduced into a probe 113 through an optical fiber 112. A base 114 is irradiated with the laser beam emitted from the probe 113. A Raman scattered light generated on the base 114 is introduced into a spectrometer 116 through the probe 113 and an optical fiber 115. In a calculating portion 117, a Raman shift is produced. In an example case in which the base 114 is a substrate having a DLC film, the carbon bonded state of the DLC film is a mixture of fine particles of SP2 (planar structure) and SP3 (tetrahedron structure). The Raman shift of the DLC film has a broad peak in the vicinity of 1300 $cm^{-1}$ to 1500 $cm^{-1}$. Since the Raman shift varies with conditions under which the DLC film is manufactured, the Raman spectrum measurement is an effective way to determine the conditions under which the DLC film is formed.

The foregoing method has been employed in the laboratory, but the Raman spectrum measurement been employed only to examine the state of bonding of molecules in a substance for forming a film on an off-line of the manufacturing process.

Off-line measurement has been performed as follows a film, which must be measured, is formed by a vacuum apparatus for forming a thin film. Then, a portion of the formed films is taken out from the film forming apparatus to be placed in a Raman spectrometer, and the measurement is performed. In the foregoing case, a DLC film having a thickness of about 10 nm and formed on a resin film having a thickness of several $\mu$m is subjected to a process in which a predetermined point of the DLC film is irradiated with a laser beam for a long time. This results in the quality of the DLC film changed due to heat, and implies that the characteristic of the film cannot sufficiently be evaluated. When the characteristic of the film is inspected off-line, a sample is obtained from a portion of the film; this obtained portion cannot be used as a product because a destructive test is performed.

In a case of the protective film 104 of the magnetic recording medium 101, which is a magnetic tape or the like, a DLC film is continuously formed on the non-magnetic support member 102 constituted by a rolled resin film having the magnetic film 103 formed on it and having a length of tens of thousands of meters. In the foregoing case, all of the factors for maintaining the constant characteristics of the film cannot easily be controlled because a great effort would required be to analyze these factors and the facility required would be too complicated. Therefore, only a minimal number of factors are controlled to maintain the constant characteristics of the film. Other factors which cannot be controlled or factors which cannot be predicted can cause the characteristics of the film to be changed, which might result in a large quantity of defective goods being produced.

Therefore, a thin-film forming method and a thin-film forming apparatus have been required with which the measured characteristics of a thin film can be feedback to the forming conditions while the characteristics of thin film are being measured in a nondestructive manner during the process for forming the thin film.

SUMMARY OF THE INVENTION

An object of the present invention is to provide a thin-film forming method and a thin-film forming apparatus with which the measured characteristic of a thin film can be fed back to the forming conditions while the characteristics of the thin film are being measured in a nondestructive manner and during the film forming process.

A thin-film forming method according to the present invention includes a thin-film forming step in which a thin film is formed on a member to be processed in a reduced-pressure atmosphere, the thin-film forming method comprising the steps of: measuring a Raman spectrum of a formed thin film; and controlling film forming conditions in accordance with a result of measurement of the Raman spectrum.

A thin-film forming apparatus according to the present invention is a thin-film forming apparatus incorporating a thin-film forming device for forming a thin film on a member to be processed in a vacuum chamber, the pressure of which has been reduced, the thin-film forming apparatus comprising: a measuring device for measuring a Raman spectrum of a formed thin film, wherein thin-film forming conditions are controlled in accordance with a result of measurement of the Raman spectrum.

The thin-film forming method and the thin-film forming apparatus according to the present invention are able to evaluate the characteristics of a formed thin film in a real-time manner by measuring the Raman spectrum. A result of the measurement of the characteristics of the thin film is immediately fed back to the forming apparatus. Thus, the thin film can always be formed under optimum conditions.

The measurement can be performed without removing a sample; the formed film can completely be used as the product.

If factors which cannot be controlled in the process for forming the thin film or factors which cannot be predicted cause the characteristics of the film to be changed, satisfactory countermeasures can be taken, which result in continuous formation of a thin film having a predetermined quality. For example, a magnetic recording medium having the protective film formed on it can be manufactured in a large quantity, and the possibility that a large quantity of defective goods are continuously manufactured can be eliminated.

DESCRIPTION OF THE PREFERRED EMBODIMENTS

A thin-film forming method and a thin-film forming apparatus according to the present invention are described below with reference to the drawings.

The present invention has a structure allowing a thin film to be formed while a Raman spectrum is being measured. When the quality of the film or the thickness of the film is changed, a measurement result is immediately fed back to control the forming conditions so as to form a thin film that always has a predetermined quality.

When a thin film is continuously formed on an elongated sheet-shape member to be processed, measurement of the Raman spectrum is performed in-line. Products having a stable quality can thus be manufactured in a large quantity.

An arbitrary thin film may be selected. Also an arbitrary forming method may be selected from sputtering, evaporation, plasma CVD, ion beam sputtering or an ion plating method. The present invention may further be applied to implantation of ions into a thin film.

A method of forming a hard carbon film (a DLC film) serving as a protective film on a magnetic film of a magnetic recording medium, such as an evaporated tape, are described below. The present invention is not limited to the foregoing operation.

The DLC film, which is a protective film for a magnetic recording medium, is formed by any one of a sputtering method, a DC plasma CVD (Chemical Vapor Deposition) method, an RF plasma CVD method, an ECR (Electron Cyclotron Resonance) plasma CVD method and an ion plating method.

The sputtering method is arranged to use a solid carbon target as the raw material. The plasma CVD method is arranged to use a hydrocarbon material in the form of a gas, such as methane, ethane or acetylene. Alternatively, a hydrocarbon in the form of liquid may be used, such as benzene, cyclohexane, toluene, xylene, methanol or ethanol, is gasified. The raw material gas may be used alone or combined with a carrier gas, such as argon.

Figure 1:
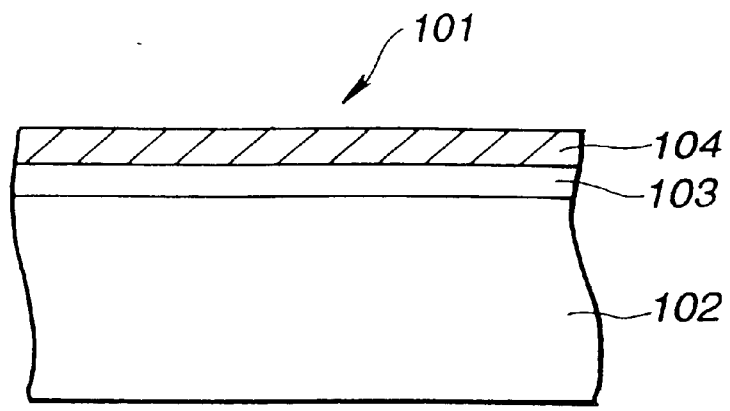
FIG. 1 is a schematic cross sectional view showing an example of a magnetic recording medium.
Figure 2:
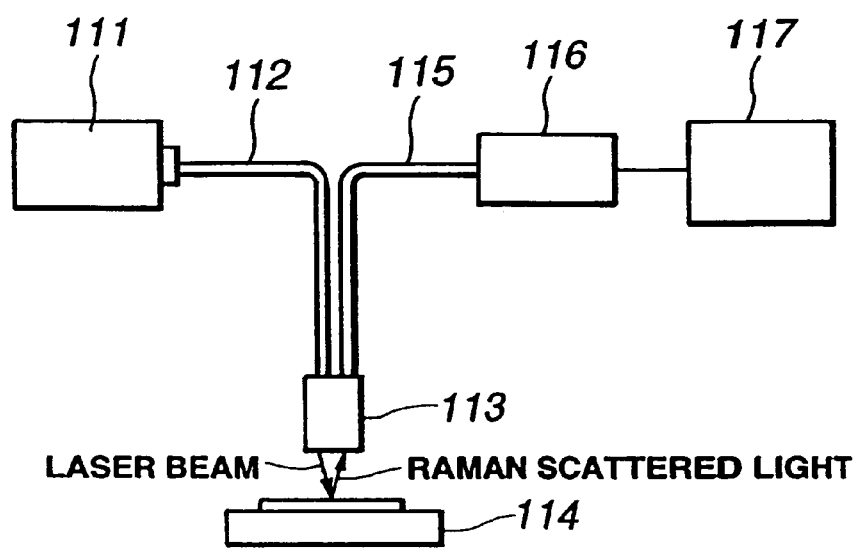
FIG. 2 is a schematic view showing a conventional Raman spectrometry.
Figure 3:
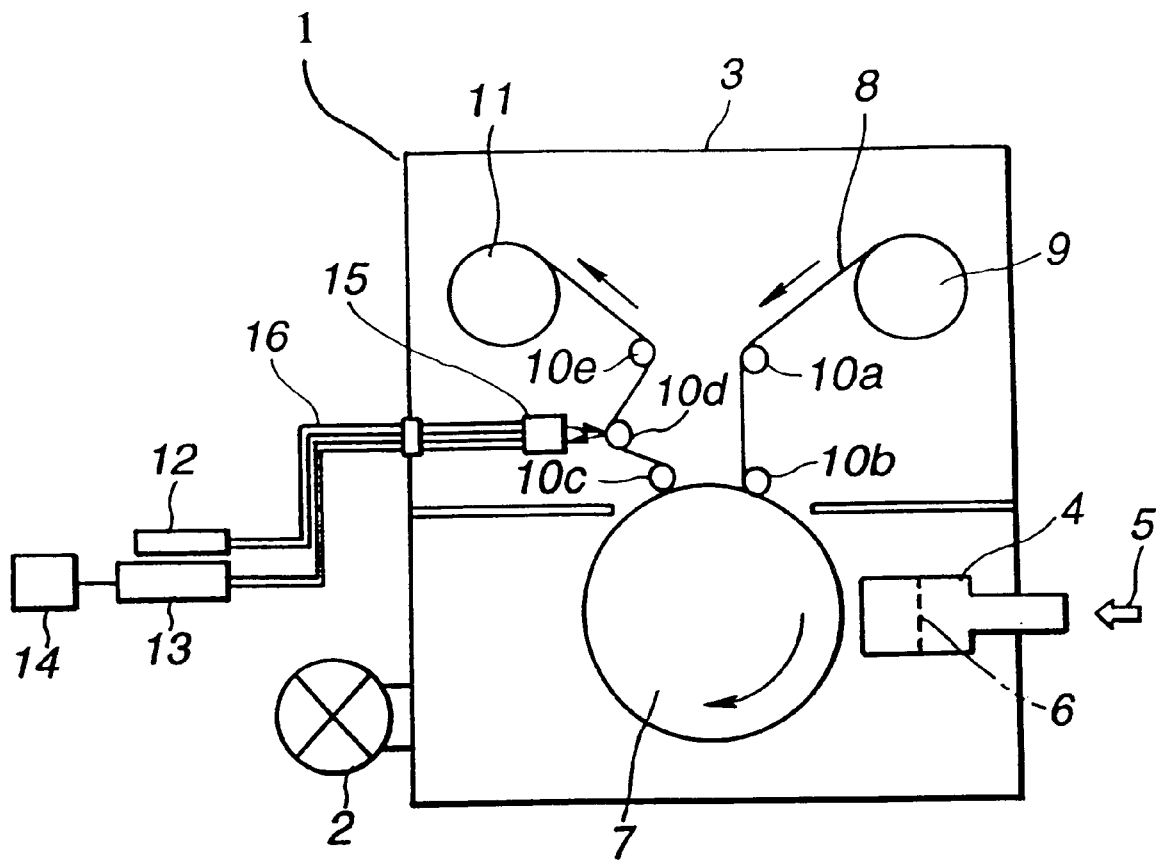
FIG. 3 is a schematic view showing an example of a thin-film forming apparatus according to the present invention.

An example of a thin-film forming apparatus for forming the DLC film is shown in FIG. 3. The thin-film forming apparatus is a thin-film forming apparatus adapted to perform RF plasma CVD.

In the RF plasma CVD apparatus 1, a raw material gas 5, such as methane or ethylene, is supplied to a reaction tube 4 disposed in a vacuum chamber 3, the inner gas of which has been discharged by a vacuum exhaust unit 2. The raw material gas 5 is formed into plasma by an RF electric field generated by of RF power supplied from an RF power source (not shown) to an electrode (a coil) 6.

The formation of plasma causes the raw material gas 5 to be decomposed. As a result, generated carbon radicals are attracted to the upper surface of an evaporated tape which serves as an opposite electrode. The carbon radicals are deposited so that a DLC film is formed.

An evaporated tape 8 to be processed has a structure such that a magnetic film, such as a thin Fe—Co film, is formed on an elongated-sheet-like or film-like non-magnetic support member made of polyethylene terephthalate. The evaporated tape 8 runs along the surface of a metal main roll 7 in the form of a cylindrical shape resulting in sequential formation of the the DLC film on the surface of the evaporated tape 8.

The evaporated tape 8 is accommodated in an unwinding roll 9 so as to be supplied to the RF plasma CVD apparatus 1. The evaporated tape 8 is moved from the unwinding roll 9 to be rotated by a can-shape main roll 7 so as to be wound around the winding roll 11 through guide rolls 10a to 10e resulting in continuous formation of the DLC film. The moving speed of the evaporated tape 8 when the DLC film is formed is, for example, about 40 m/minute to 100 m/minute. The thickness of the formed DLC film is about 5 nm to about 20 nm.

The RF plasma CVD apparatus 1 has the above-mentioned basic structure. In the present invention, a Raman spectroscope is joined to the RF plasma CVD apparatus 1. The Raman spectrum of the formed DLC film is measured in-line. When the quality or the thickness of the film is changed, feedback is immediately performed to control the film forming conditions.

The Raman spectroscope incorporates a laser oscillator 12 for emitting a laser beam, a spectrometer 13 for spectral-analyzing Raman scattered light which is returned light, a calculating device 14 for converting a measurement result into a measure of the quality or the thickness of the film in order to calculate optimum film forming conditions, and a probe 15 incorporating an objective lens and arranged to irradiate the evaporated tape 8 (on which the DLC film has been formed,) with a laser beam so as to collect Raman scattered light. In the vacuum chamber 3, the probe 15 is disposed opposite to the evaporated tape 8 on which the DLC film has been formed.

In this embodiment, a laser beam is (with the aid of a guide roll 10d) substantially perpendicularly emitted from the probe 15 toward the evaporated tape 8.

The laser oscillator 12 and the spectrometer 15 are optically connected to the probe 15 through optical fibers 16. The laser beam emitted from the laser oscillator 12 is introduced into the probe 15 through the optical fiber 16 to irradiate the DLC film formed on the surface of the evaporated tape 8. Raman scattered light reflected by the DLC film is collected by the probe 15 to be introduced into the spectrometer 13 through the optical fiber 16.

In a case of the DLC film, a broad peak is displayed in the vicinity of Raman shifts 1300 $cm^{-1}$ to 1500 $cm^{-1}$. The Raman shift of the DLC film is changed depending on the film forming conditions, and this change corresponds to the change in the quality of the formed film. Data representing the film forming conditions can thus be obtained.

The foregoing apparatus is arranged to always monitor the Raman spectrum. If a change occurs, a result is fed back to the RF plasma CVD apparatus 1 so that the film forming conditions are reset to optimum values.

It is preferable that the Raman spectrum sampling period is between 10 seconds and 150 seconds. If the sampling period is too short, the peak becomes oblique and excessive noise is produced. If the sampling time is too long, the object for evaluating the quality of the film in a real-time manner cannot be achieved. The laser power of the laser oscillator 12 is about 4 mW to about 1 W.

If the Raman spectrum is changed, the film forming conditions are controlled so they may be restored. Thus, a DLC film having a predetermined quality and a predetermined thickness can always be formed. The film forming conditions which must be controlled include a flow rate of reaction gas, the ratio of raw material gas and carrier gas, the pressure in the reaction chamber and voltage. When methane raw material gas and argon carrier gas are employed, reduction in the ratio of methane causes decomposition in the plasma to be enhanced, resulting in change the quality of the formed DLC film. When the distance from the reaction tube 4 to the main roll 7 is adjusted, the difference between the pressure in the reaction tube 4 and the outside portion of the same is changed and the quality of the formed DLC film is changed as well.

Therefore, control which is performed in accordance with a result of the measurement of the Raman spectrum enables a DLC film having a predetermined quality to be formed.

The quality of the DLC film exerts a great influence on the durability (still durability and shuttle durability), the friction factor, density, and the rutstproofing characteristic of the obtained evaporated tape. It is a very important factor to maintain the foregoing quality when the quality of the evaporated tape is maintained.

Figure 4:
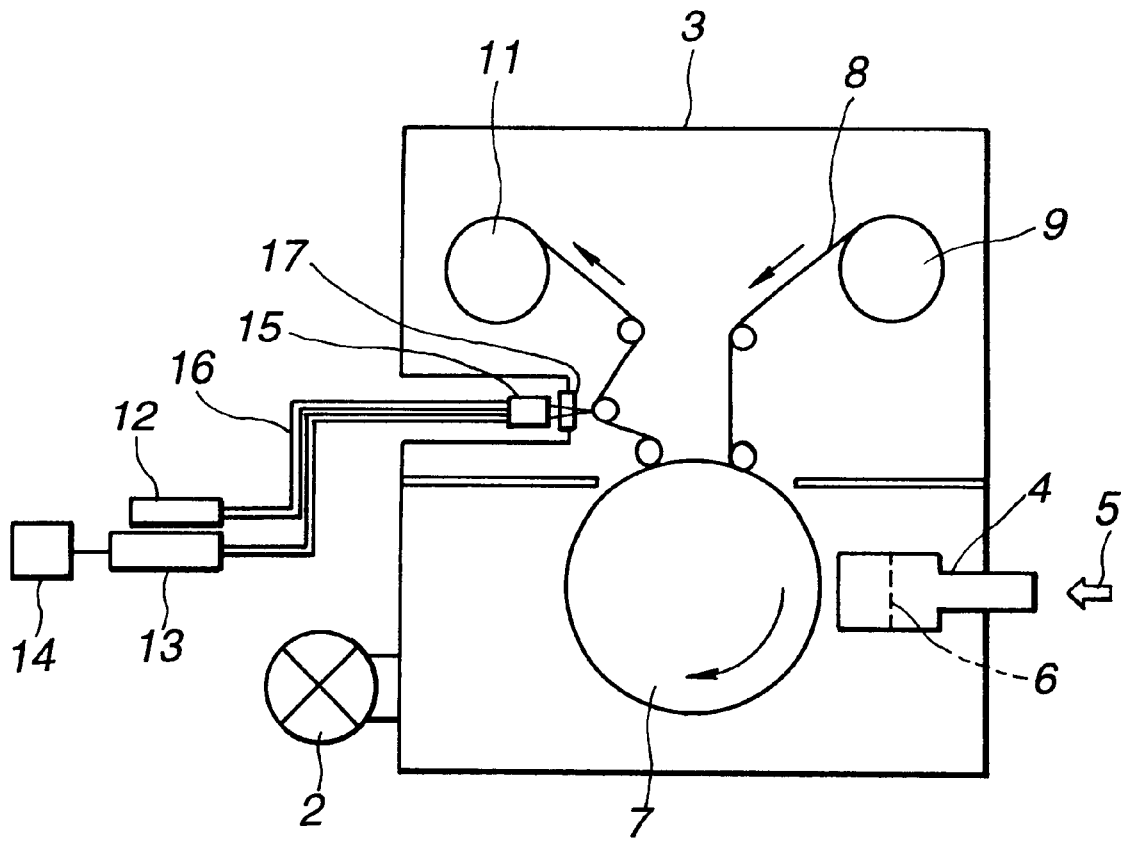
FIG. 4 is a schematic view showing another example of a thin-film forming apparatus according to the present invention.

FIG. 4 shows another example of the RF plasma CVD apparatus according to the present invention which has the same basic structure as that of the apparatus shown in FIG. 3, but differs in that the probe 15 is disposed on the outside of the vacuum chamber 3.

When the probe 15 is required to be on the outside to easily handle the probe 15 or to prevent adhesion of a substrate for use to form the film to the probe 15, the probe 15 may be joined to the outside portion of the vacuum chamber 3.

In this case, a laser beam or Raman scattered light is applied or introduced from the laser oscillator 12 through a window 17 provided for the vacuum chamber 3.

The RF plasma CVD apparatus having the above-mentioned structure also has the structure that the probe 15 is, at the position of the guide roll 10d, disposed opposite to the evaporated tape 8. It is preferable that the probe 15 is disposed at a position (e.g., the position of the guide roll) at which the shift is not considerably changed (±5 $\mu$m or smaller). In practice, however, sometimes the position of the guide roll cannot be selected because of a some structural limitation of the film forming apparatus.

In this case, a position, (such as the position of the cooling main roll 7) at which a great shift takes place is undesirably selected. The cylindricity of the main roll 7 is about ±50 $\mu$m. In the above-mentioned range, the distance from the probe 15 to the surface on which the DLC film is formed is changed. To maintain a constant intensity of the Raman spectrum, the foregoing distance must be constant. Therefore, a mechanism must be employed such that, for example, a uniaxial stage is provided which maintains the predetermined distance.

Figure 5:
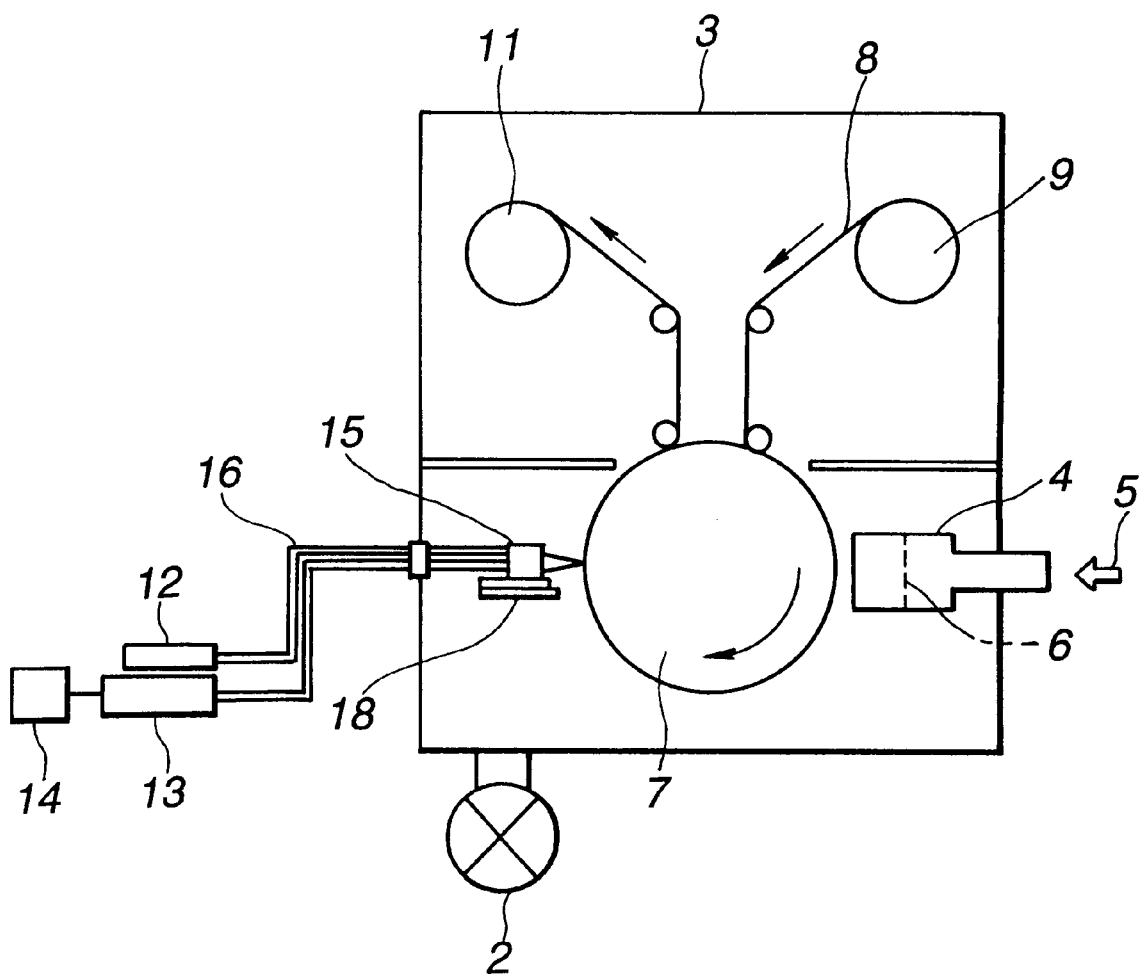
FIG. 5 is a schematic view showing an example of a thin-film forming apparatus incorporating a probe provided with a focal-point control mechanism.

FIG. 5 shows an example of a RF plasma CVD apparatus structured such that the probe 15 is disposed at the position of the main roll 7 to be opposite to the evaporated tape 8. In this example, the probe 15 is mounted on a support unit 18 which is movable in a direction in which the support unit 18 approaches and recedes from the main roll 7. Moreover, a focal-point control mechanism for maintaining a predetermined distance is provided.

Figure 6:
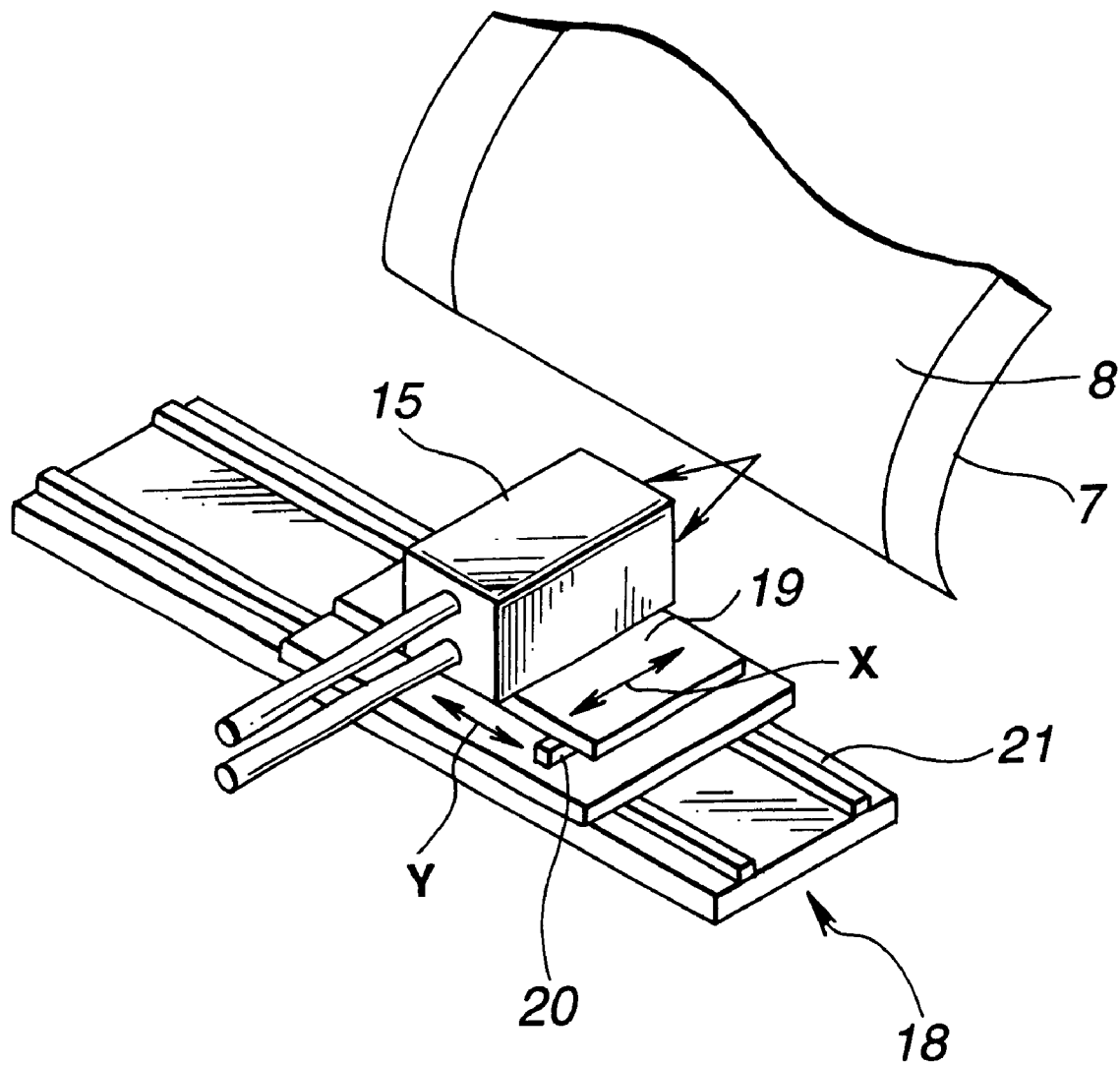
FIG. 6 is a perspective view showing the schematic structure of a focal-point control mechanism.

As shown in FIG. 6, the support unit 18 incorporates a table 19 on which the probe 15 is mounted. Moreover, the support unit 18 incorporates a first linear slider 20 for moving the table 19 in a lengthwise direction (as indicated with arrow X) in which the table 19 approaches and recedes from the main roll 7. In addition, the support unit 18 incorporates a second linear slider 21 which is moved in a widthwise direction (indicated with arrow Y) of the evaporated tape 8.

When the probe 15 on the table 19 is canned in the X direction by the first linear slider 20, the focal point of the probe 15 is controlled. When the second linear slider 21 is operated to perform scanning in the Y direction, measurement can be performed-at an arbitrary position in the widthwise direction of the evaporated tape 8.

The foregoing focal-point control mechanism may comprise, for example, a known auto-focusing mechanism or a structure using a displacement gauge, for example, a laser displacement gauge. When the focal-point control mechanism together with the probe 15 is mounted on the table 19, the objective lens of the probe 15 can always be focused to the DLC film on the surface of the evaporated tape 8.

Figure 7:
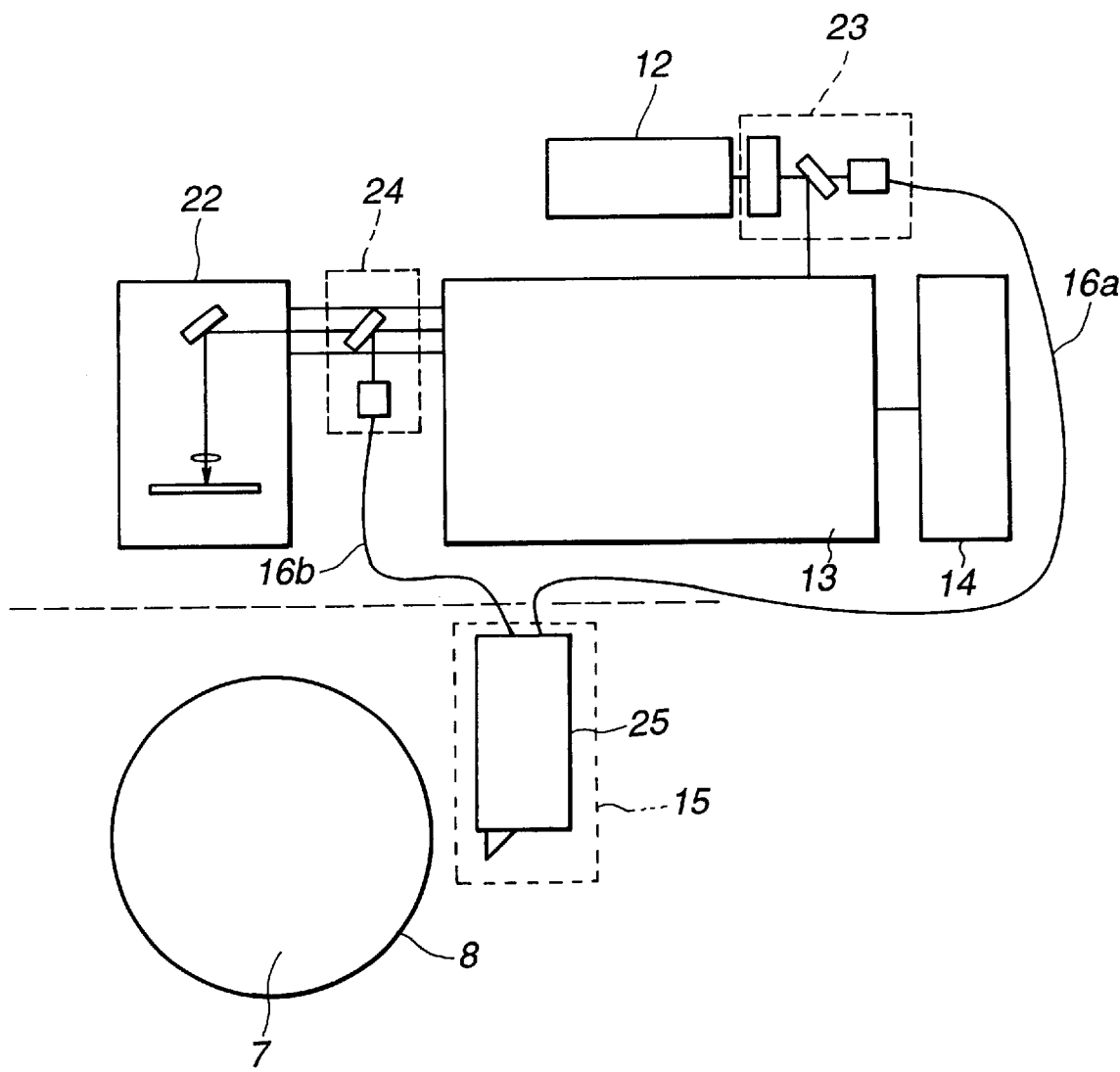
FIG. 7 is a schematic view showing the structure of a Raman spectroscope.

A general-purpose apparatus, such as that shown in FIG. 7, may be employed as the Raman spectroscope for measuring the Raman spectrum, in which an optical system must individually be provided in order to cause the probe 15 to emit the laser beam and fetch Raman scattered light.

FIG. 7 shows a measuring apparatus for performing Raman spectrometry of a typical example. This apparatus incorporates the laser oscillator 12, the spectrometer 13 and a microscope 22. A typical sample is set to the microscope 22 so that Raman spectral analysis is performed.

A conversion optical system 23 and an optical fiber 16a are provided which introduce the laser beam emitted from the laser oscillator 12 to the probe 15. Moreover, an optical fiber 16b and a conversion optical system 24 are provided which introduce Raman scattered light fetched through the probe 15 into the spectrometer 13.

The probe 15 has a converting optical system which is connected to the leading end of each of the optical fibers 16a and 16b. Usually, the probe 15 as well as incorporates a fiber head 25 having a filter or the like which permits selective penetration of only Raman scattered light.

In consideration of the foregoing focal-point control mechanism for the measuring apparatus having the above-mentioned structure, the fiber head 25 may be mounted on the table 19 to control the movement of the probe 15. However, employment of this structure is disadvantageous when considering its response characteristics. Since the fiber head 25 is a large and heavy device, the size of the support unit 18 must be enlarged to mount the fiber head 25. Moreover, the response speed cannot easily be raised.

Therefore, this embodiment is structured such that only the converting optical system which is joined to the leading end of the fiber head 25 in the probe 15 is mounted on the table 19. Thus, enlarging of the apparatus can be prevented and control of the focus point can be performed quickly.

Figure 8:
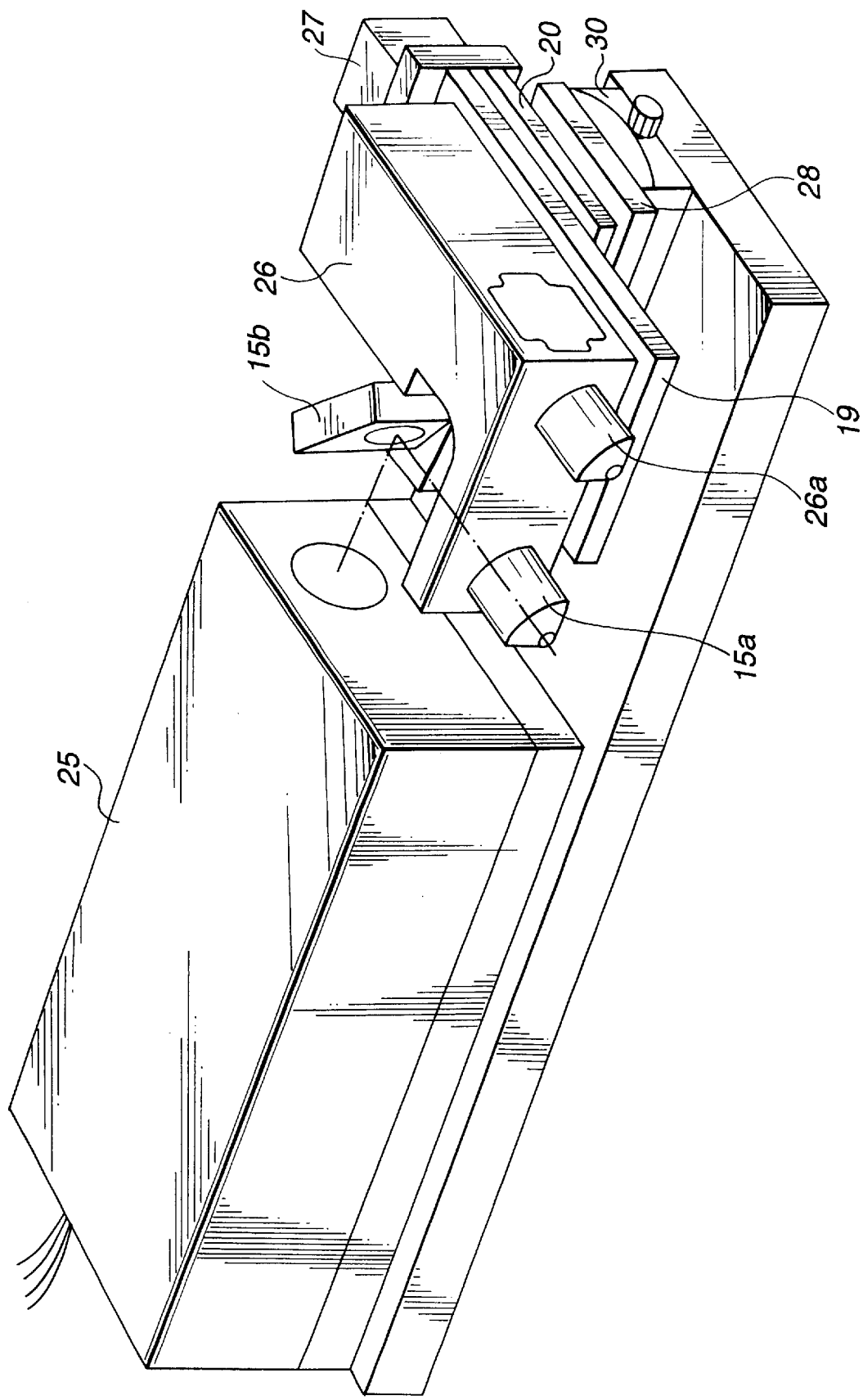
FIG. 8 is perspective view showing a structure for joining a fiber head of a Raman spectroscope and a probe to each other.
Figure 9:
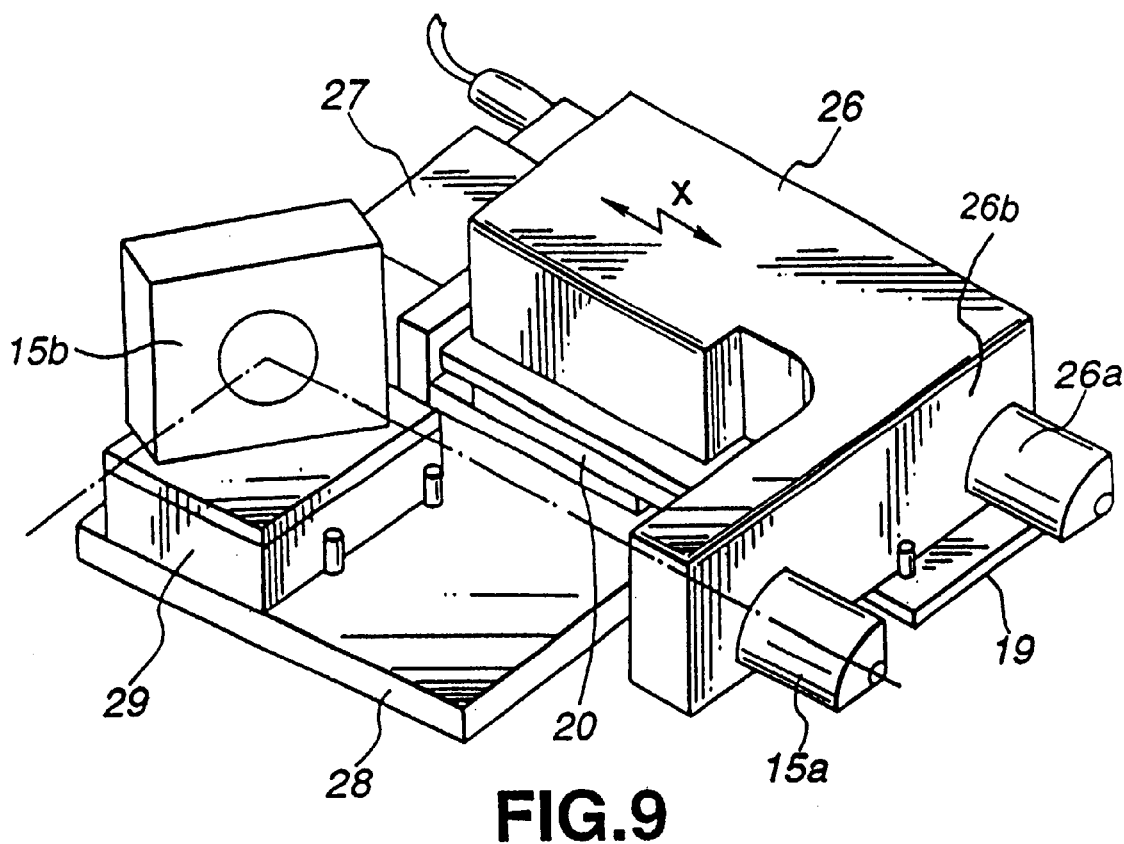
FIG. 9 is a perspective view showing an example of a structure for joining the probe to the focal-point control mechanism.
Figure 10:
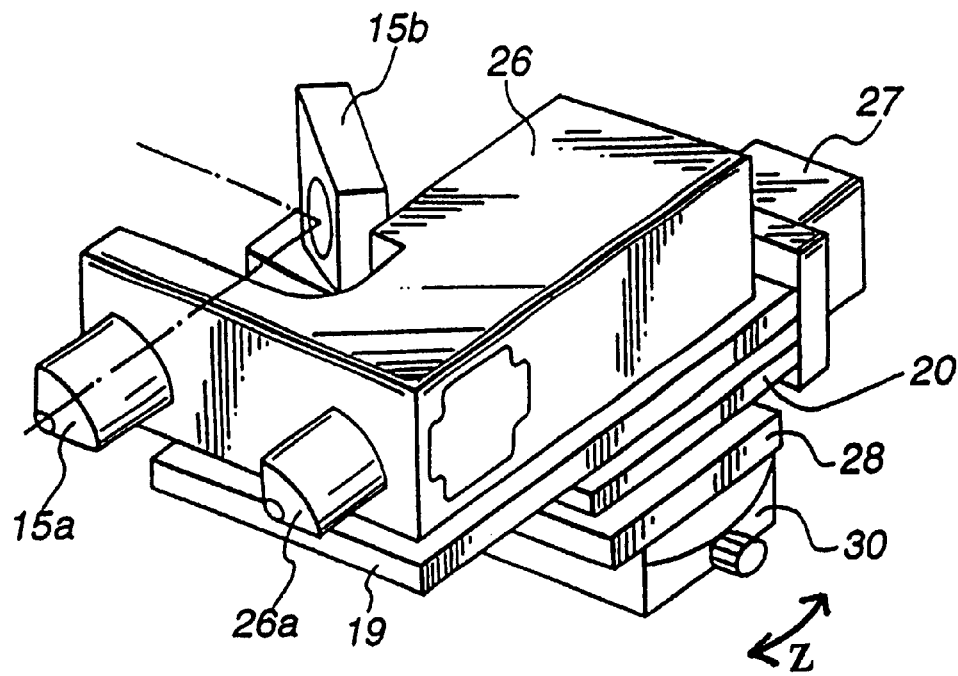
FIG. 10 is a perspective view showing the structure for joining the probe to the focal-point control mechanism when the structure is viewed from a different angle.

FIGS. 8 to 10 show an example of a focal-point control mechanism having the above-mentioned structure.

As shown in FIG. 8, the foregoing focal-point control mechanism has the structure that the fiber head 25 is secured. Moreover, only the conversion optical system of the probe 15 (in FIG. 7) is mounted on the table 19.

The conversion optical system of the probe 15 incorporates an objective lens 15a and a Raman mirror 15b. Only the objective lens 15a is mounted on the table 19. The laser beam emitted from the laser oscillator 12 (in FIG. 7) is applied through the fiber head 25. The laser beam is reflected by the Raman mirror 15b in a way that applies it to the DLC film through the objective lens 15a. Raman scattered light transmitted from the DLC film is fetched by the objective lens 15a, and then reflected by the Raman mirror 15b. Then, the Raman scattered light is introduced into the spectrometer 13 (in FIG. 7) through the fiber head 25.

FIGS. 9 and 10 show a mechanism for controlling the objective lens 15a by operating the auto-focusing mechanism. An objective lens 26a for auto-focusing and the objective lens 15a of the probe 15 are, in parallel, disposed on a front panel 26b of the auto-focus mechanism 26. These elements are synchronously moved in the X direction by the first linear slider 20 which incorporates a rotating motor 27. In response to a control signal supplied from the auto-focus mechanism 26, the rotating motor 27 moves the second linear slider 21 in the X direction.

The first linear slider 20 is disposed on the fixed plate 28, and the Raman mirror 15b is secured to the fixed plate 28.

The Raman mirror 15b is, through a spacer 29, secured to a position at which an optical axis of the objective lens 15a and the optical axis of the fiber head 25 intersect at right angles.

The fixed plate 28 is, as shown in FIG. 10, disposed on a swivel stage 30. When the swivel stage 30 is rotated in a direction indicated with an arrow Z, the movement angles of the objective lens 15a and the objective lens 26a for auto-focusing can be adjusted. When the movement angles are adjusted, the angles of the objective lens 15a and the objective lens 26a for auto-focusing can be adjusted to be perpendicular with respect to the evaporated tape 8 (which is the member to be processed).

Figure 11:
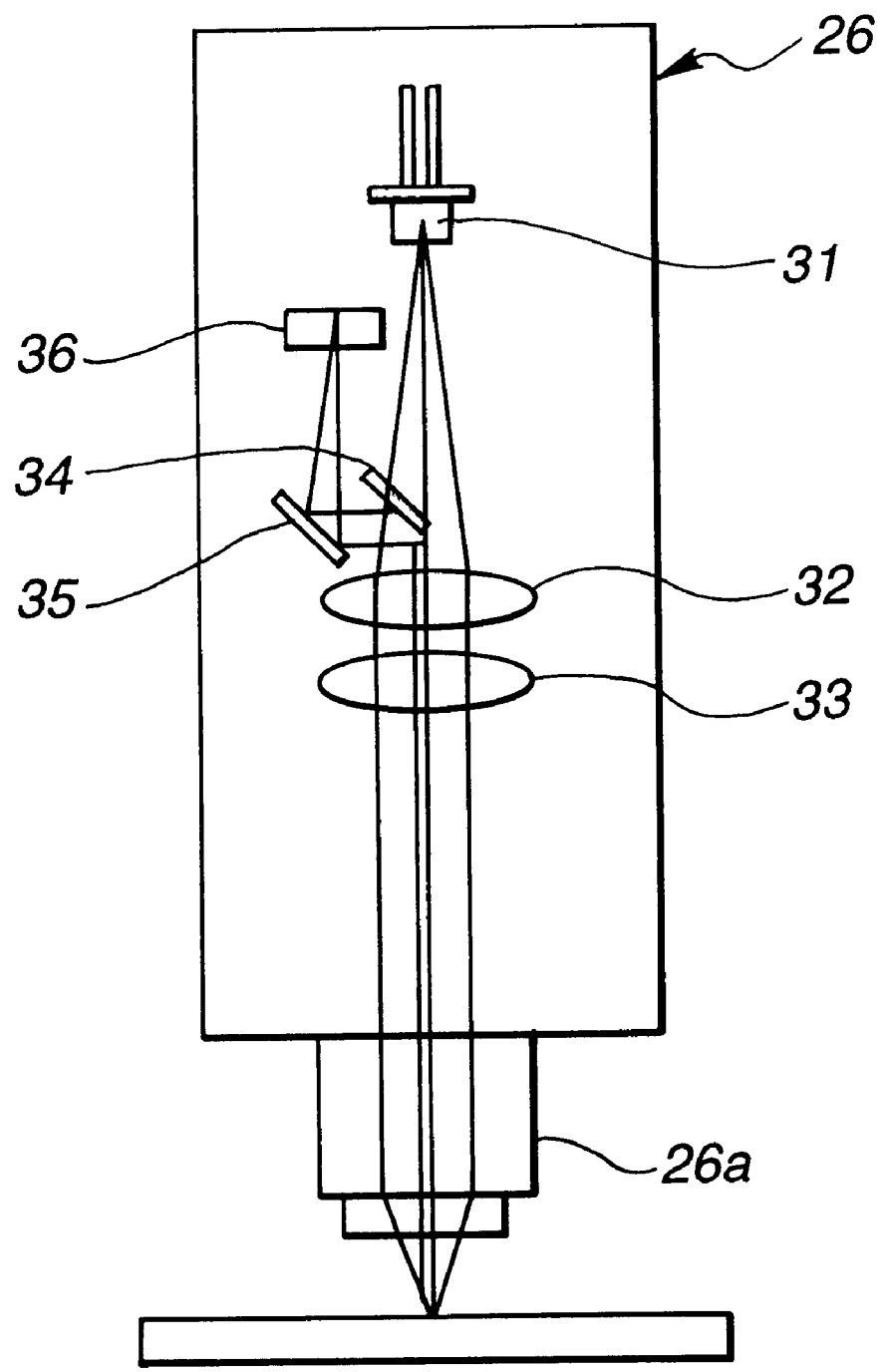
FIG. 11 is a schematic view showing an example in which a general-purpose focal-point control mechanism is used.

The auto-focus mechanism 26 is a general-purpose auto-focus mechanism. For example, as shown in FIG. 11, a laser beam emitted from a laser diode 31 is emitted from the front panel 26b through focus lenses 32 and 33. Reflected light is introduced into a two-piece diode 36 through a knife edge 34 and a mirror 35. The position of the front panel 26a is controlled in accordance with an output of the two-piece diode 36.

The foregoing focal-point control mechanism can have the structure that only the light-weight objective lens 15a is mounted on the first linear slider 20, reducing the size of the apparatus and allowing high speed response. As a result, a constant distance can always be maintained from the objective lens 15a of the probe 15 to the evaporated tape 8, which is the member to be processed.

Figure 12:
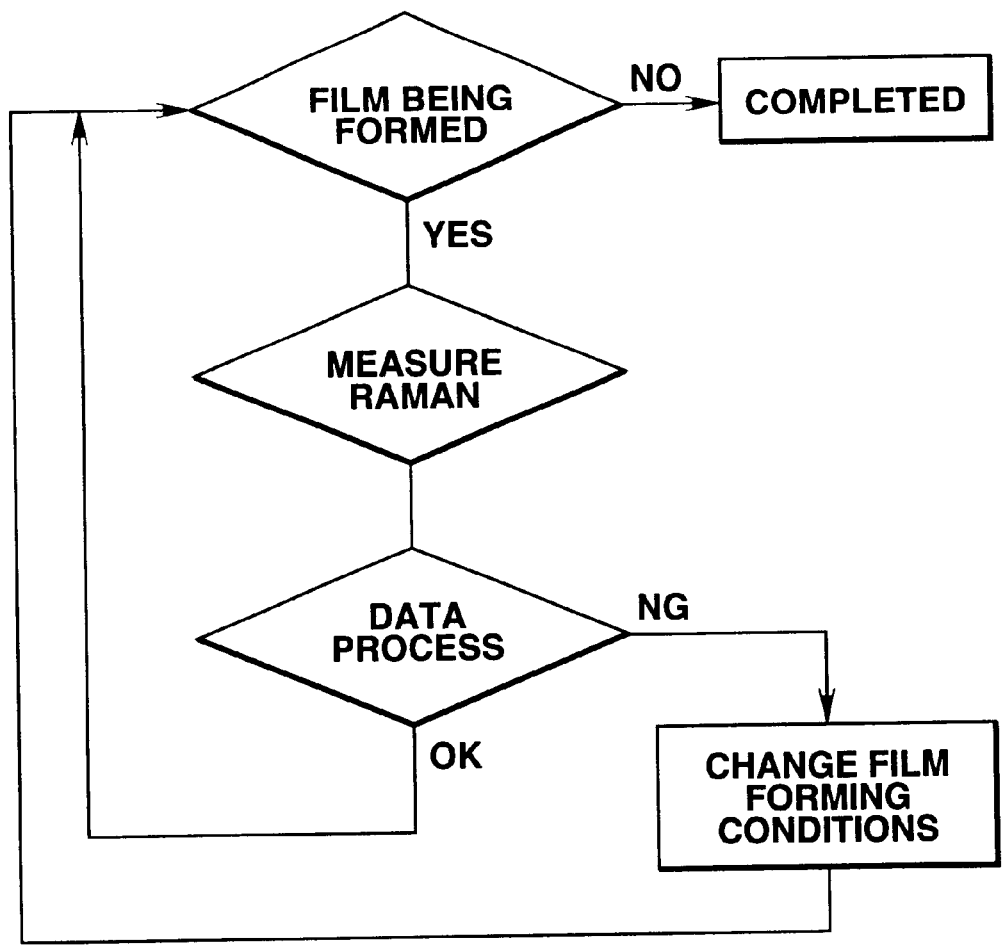
FIG. 12 is a flow chart of a process for forming a thin film.

FIG. 12 is a flow chart of a process for forming a thin film. During the process for forming a film, the Raman measurement and the data process are continuously performed. If a change in the quality of the film is confirmed in accordance with a result of the measurement, the film forming conditions are immediately changed. Also, a focusing operation is continuously performed during the foregoing process.

A trial apparatus was able to realize a control accuracy of the focal point of ±10 μm and a Raman intensity accuracy of ±3% when samples of the auto-focusing were performed at intervals of 0.5 second to one second, resulting in an accuracy of the film thickness of ±3%.

Each of the thin-film forming apparatus incorporates only one probe 15 of the Raman spectroscopy. Moreover, the probe 15 is scanned for the widthwise distance of the evaporated tape 8. Note that a plurality of the probes 15 may be disposed in the widthwise direction of the evaporated tape 8, which states of a plurality of portions in the widthwise direction of the evaporated tape 8 in which the thin film is formed can be analyzed in parallel, allowing more precise control.

Figure 13:
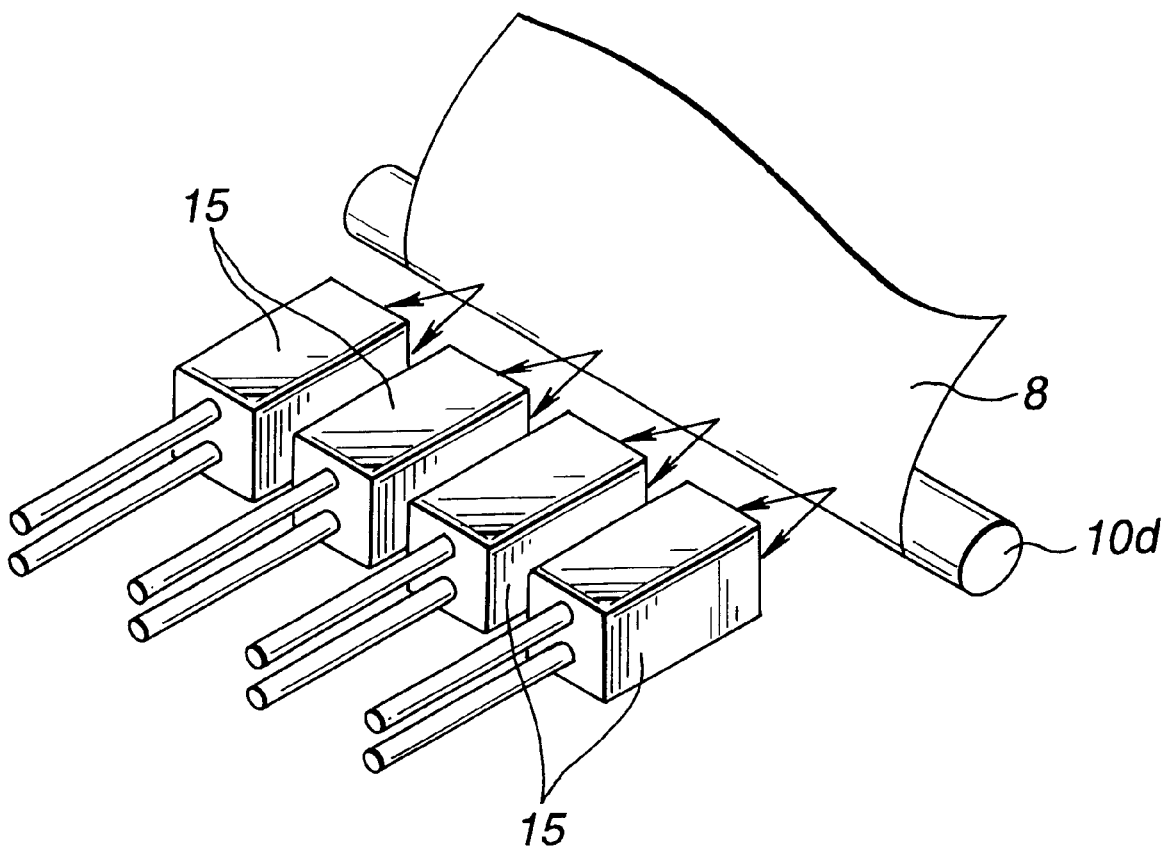
FIG. 13 is a schematic perspective view showing an essential portion of a state in which a plurality of probes have been mounted on the focal-point control mechanism.

FIG. 13 shows a state in which a plurality of the probes 15 are disposed in a case in which the probes 15 are secured opposite to the guide roll 10d. In this embodiment, four probes 15 are disposed.

Figure 14:
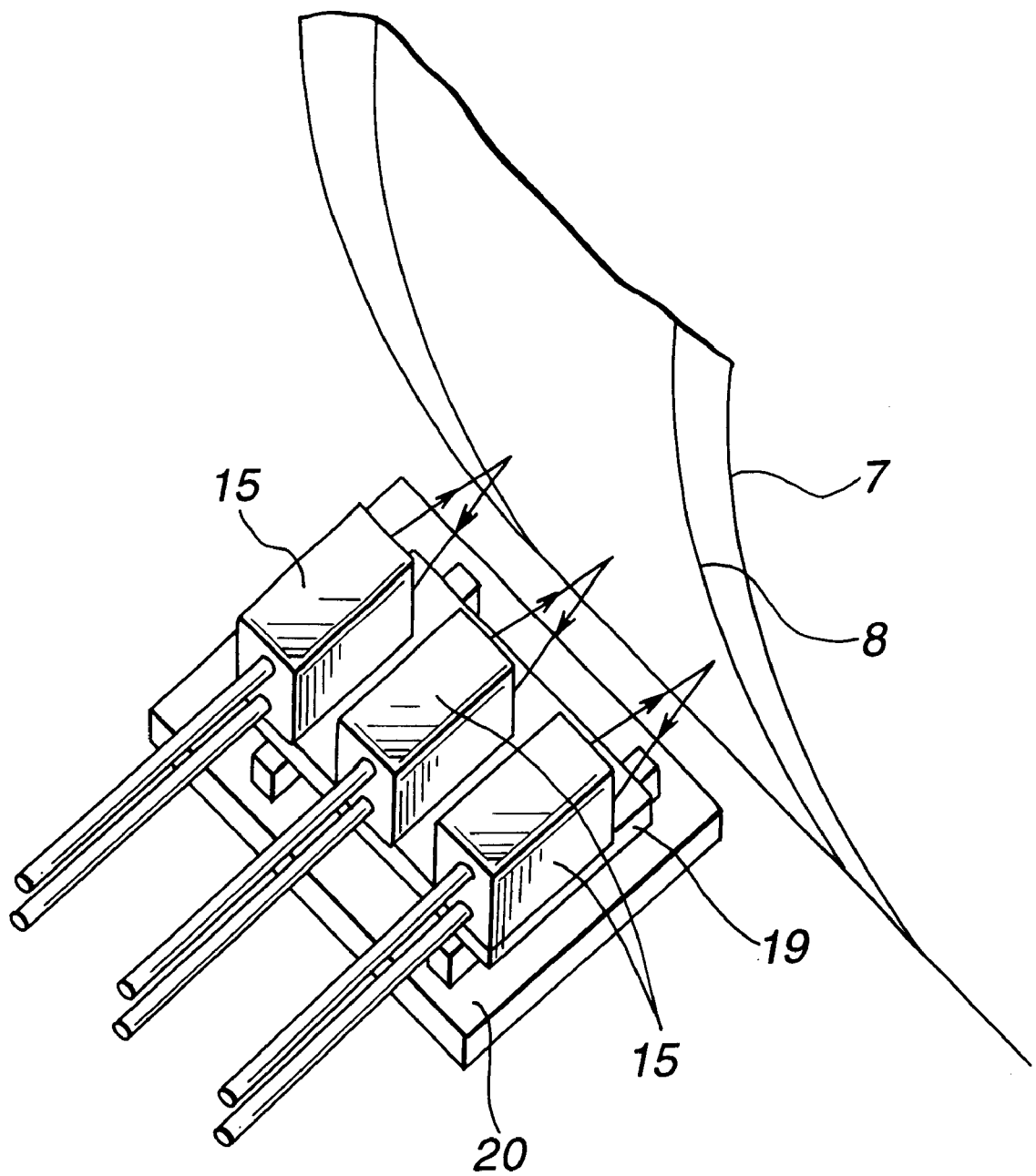
FIG. 14 is a schematic perspective view showing an example of a thin-film forming apparatus provided with a Raman spectroscope having a variable output laser oscillator.

FIG. 14 shows an example in which the focal-point control mechanism is provided. In this example, three probes 15 are disposed on the table 19, the position of which is controlled by the auto-focus mechanism.

The thin-film forming apparatus according to the present invention is required to maintain a predetermined intensity of the Raman shift. To realize this requirement, it is effective to provide the focal-point control mechanism as described above. Note that the adjustment speed of the uniaxial stage must be raised as the film forming speed is raised. This adjustment speed has a limitation, therefore excessively high film forming speed inhibits the foregoing focal-point control mechanism to easily follow such a high speed. Another problem arises in that heat is undesirably generated because the process is performed in a vacuum.

In the above, the output of the laser beam from the laser oscillator 12 (FIG. 7) which constitutes the Raman spectroscope may be controlled, making constant the Raman intensity reflected from the DLC film.

Figure 15:
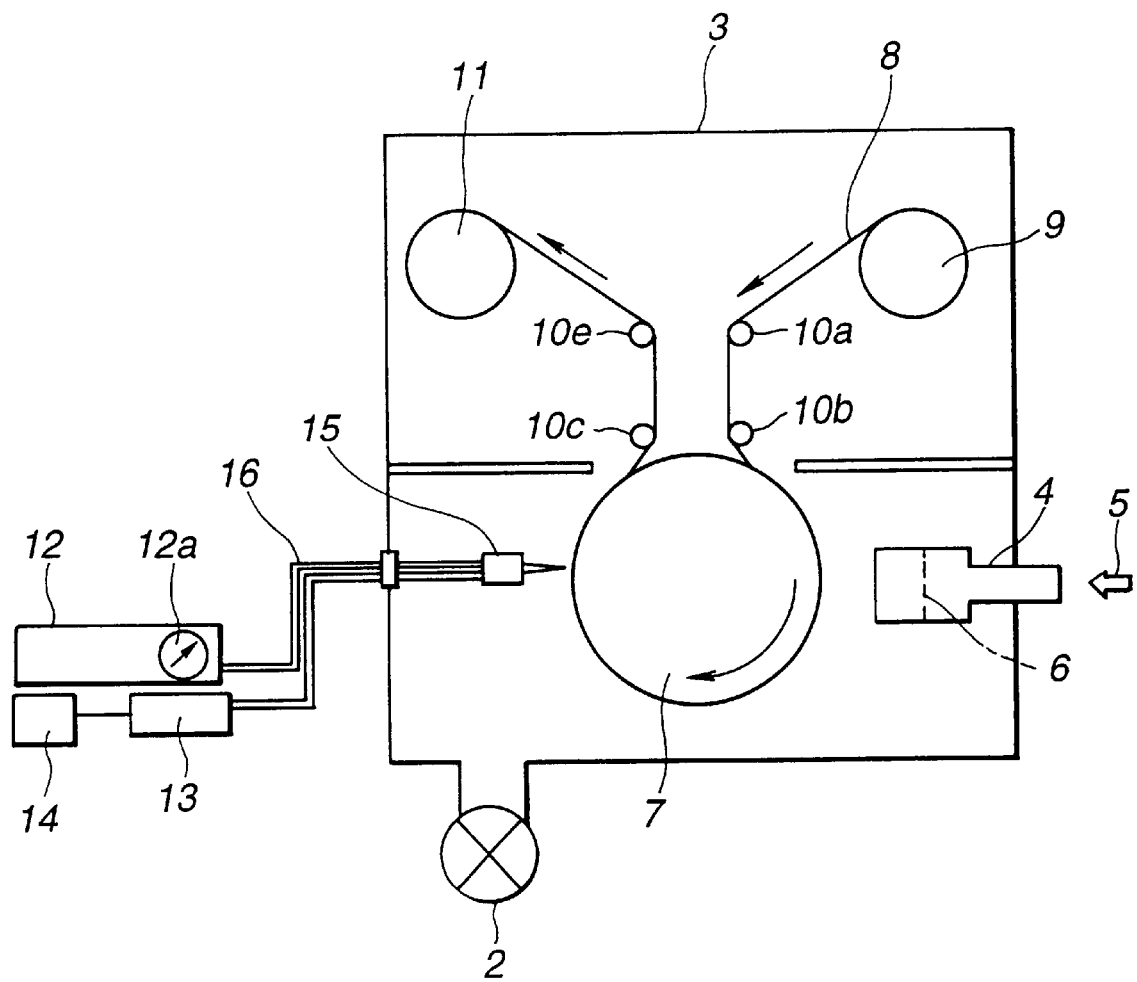
FIG. 15 is a schematic view showing a structure for joining the probe for controlling output of a laser.

FIG. 15 shows an example of a RF plasma CVD apparatus in which an output adjustment mechanism 12a is provided for the laser oscillator 12 which constitutes the Raman spectroscope. The basic structure of the foregoing RF plasma CVD apparatus is the same as the apparatus shown in FIG. 5 (the structure of the foregoing apparatus is omitted from description). Note that the probe 15 is secured and the focal-point control mechanism is not provided.

Figure 16:
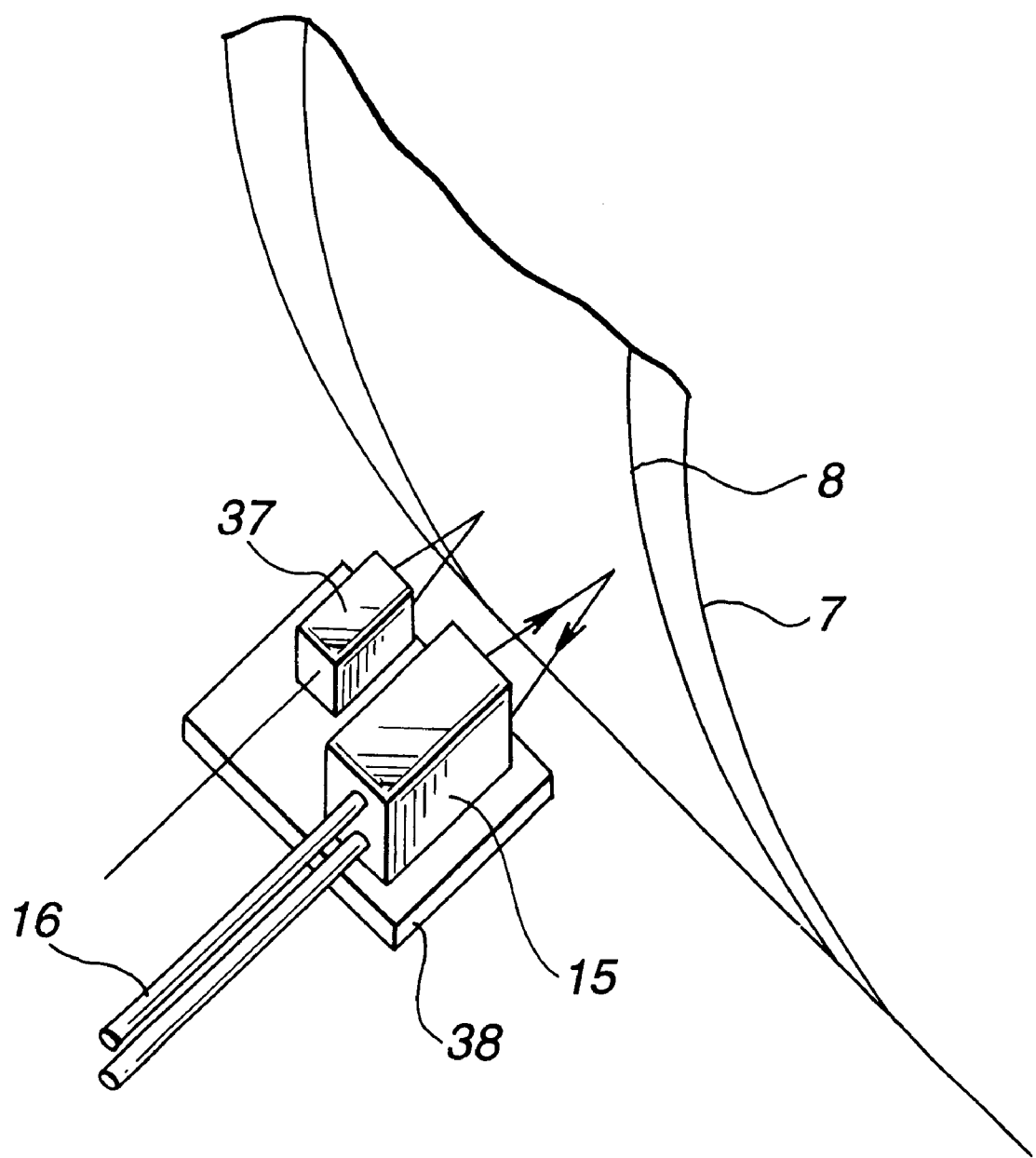
FIG. 16 is a schematic perspective view showing an example in which a displacement gauge adjacent to the probe is disposed on a base plate.

As shown in FIG. 16, the RF plasma CVD apparatus shown in FIG. 15 has a structure that a displacement gauge 37 is disposed on the base plate 38 at a position adjacent to the probe 15. In accordance with information supplied from the displacement gauge 37, the output of the laser beam from the laser oscillator 12 is controlled. When a change in the distance from the probe 15 to the evaporated tape 8 has been observed by the displacement gauge 37, this information is immediately fed back to the output adjustment mechanism 12a. The laser output is thus adjusted in such a manner that results in a constant Raman intensity reflected by the DLC film.

Figure 17:
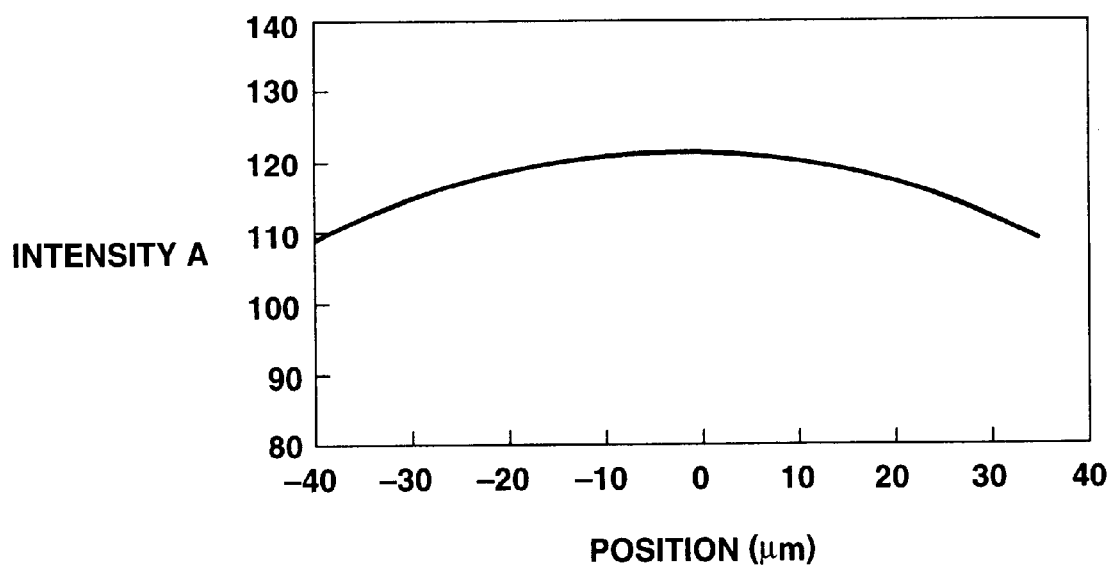
FIG. 17 is a graph showing the relationship between the distance (the position) between the probe and the thin film and the intensity of an applied laser beam.

FIG. 17 shows the relationship between the difference in the direction from the probe 15 to the main roll 7 from a reference position and intensity A of scattered light. If the foregoing distance is deviated from the foregoing reference position (The position of the focal point of the objective lens 15a), the intensity A of scattered light is lowered.

Figure 18:
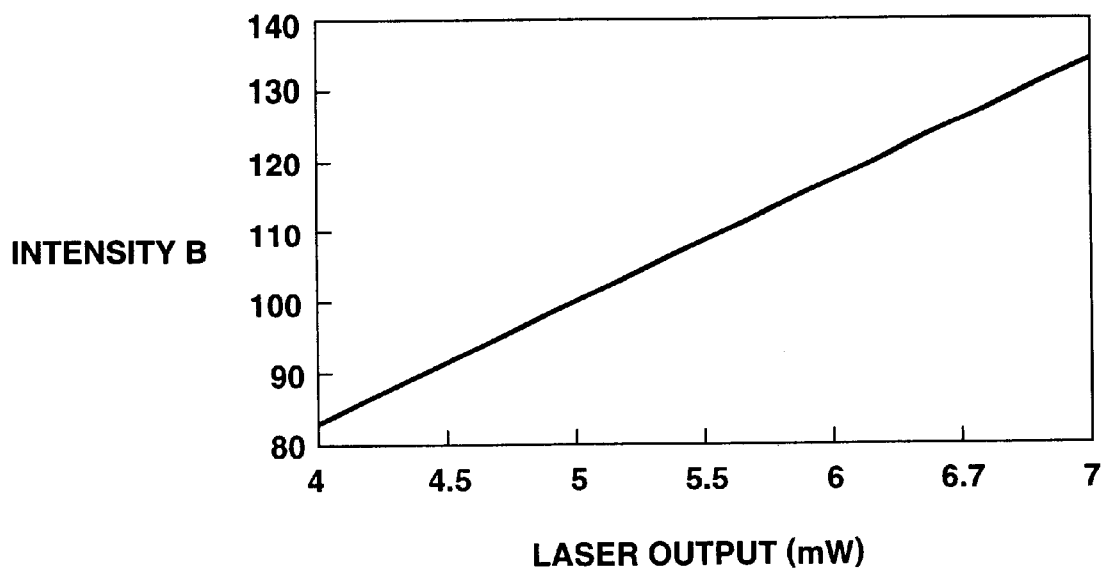
FIG. 18 is a graph showing the relationship between output of a laser beam and the intensity of the applied laser beam.

If the laser output is enlarged as shown in FIG. 18, the intensity B of the laser beam which must be applied is raised.

Therefore, the output of the laser beam is adjusted by a method with which, for example, the following control is performed:

intensity A (position)×intensity B (laser beam output)= constant

This allows the output adjustment mechanism 12a to be controlled to adjust the output of the laser beam.

In accordance with this equation, the intensity B (that is, the output of the laser beam) is changed to correspond to a shift of the position and a change in intensity making the value of the foregoing product constant. As described above, an adjustment for following is performed.

When this adjustment is performed, a change in the intensity of scattered light caused from change in the distance from the probe 15 to the main roll 7 can be compensated for. Since the intensity of the scattered light is made to be constant, a change in the Raman intensity can be reduced, resulting in stable measurement results.

The control realized by adjusting the laser output has advantages in that no mechanical operation is required, the apparatus does not become too complicated, cost growth can be prevented and satisfactory high speed response can be realized.

The adjustment of the laser output may be performed by a structure obtained by combining an RF plasma CVD apparatus with the foregoing focal-point control mechanism.

Figure 19:
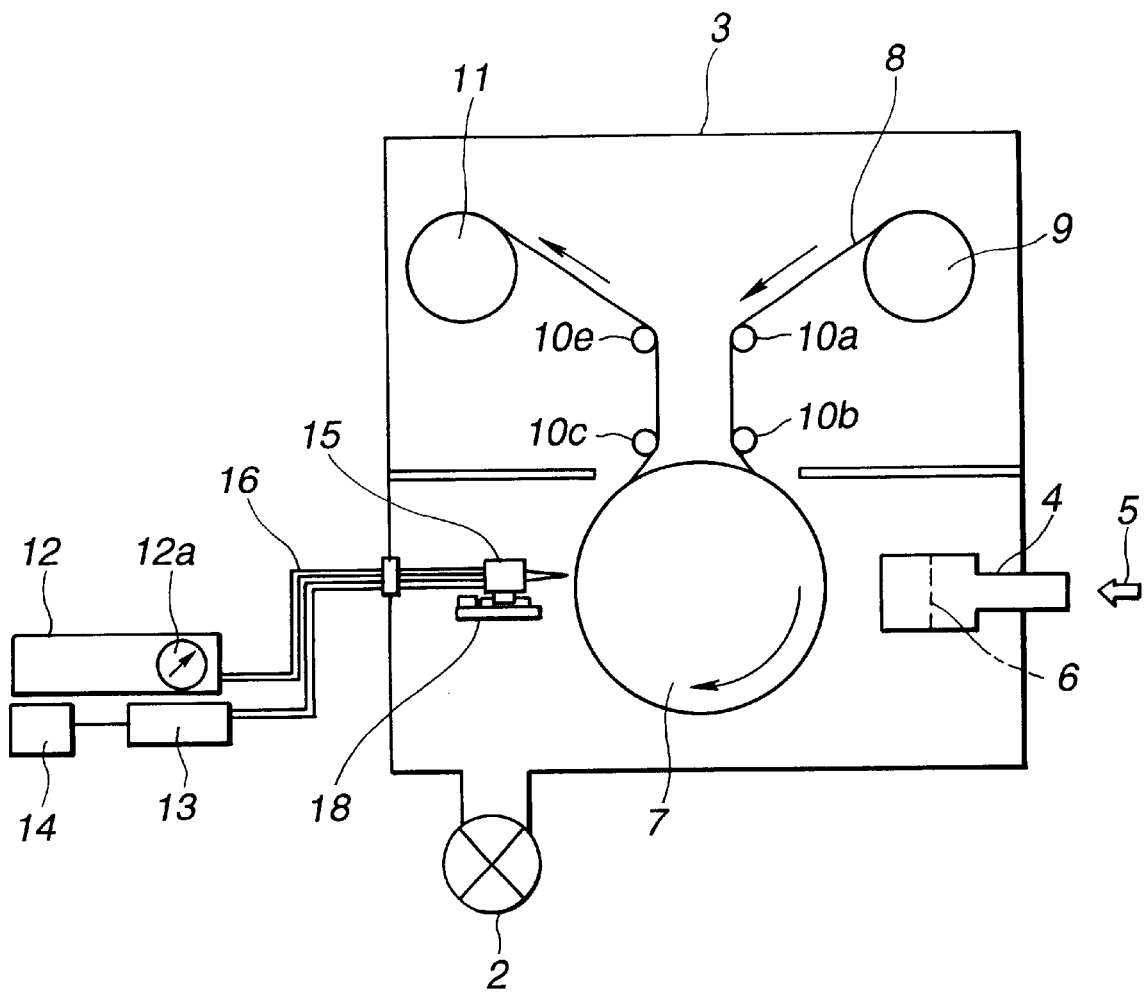
FIG. 19 is a schematic view showing an example of a thin-film forming apparatus formed by combining the variable output laser oscillator and the focal-point control mechanism with each other.

FIG. 19 shows an example of a RF plasma CVD apparatus in which the probe 15 is placed on a support unit 18 provided with the focal-point control mechanism. Moreover, the output adjustment mechanism 12a is provided for the laser oscillator 12 of the Raman spectroscope.

In this arrangement, a relatively slow one the distance, such as change in caused from a change in the dimension of the main roll 7 occurring because the temperature has been changed, is overcome by the focal-point control mechanism. In a case of a quick change, such as a change in the distance which occurs during high speed rotation which takes place due to insufficient accuracy (cylindricity) of the main roll 7, is overcome by adjusting the laser output.

Also, the foregoing RF plasma CVD apparatus in which the output adjustment mechanism 12a is provided for the laser oscillator 12 of the Raman spectroscope may have a structure that a plurality of the probes 15 are disposed in the widthwise direction of the evaporated tape 8.

The above-described system and method are illustrative of the principles of the present invention. Numerous modifications and adaptations will be readily apparent to those skilled in this art without departing from the spirit and scope of the present invention.

What is claimed is:

1. A thin-film forming method comprising the steps of:
   providing a Raman spectrometer having a probe;
   forming a thin film on a member that is moving in-line;
   controlling a focal point of said probe while said thin film is moving in line;
   measuring a Raman spectrum of said formed thin film while said thin film is moving in-line and producing a result;
   controlling film forming conditions in accordance with said result of said measurement of the Raman spectrum.

2. A thin-film forming method according to claim 1, wherein said step of measuring the Raman spectrum is performed while continuously forming the thin-film on said member, wherein said member is an elongated sheet member.

3. A thin-film forming method according to claim 1, wherein said thin film is a protective film of a magnetic recording medium.

4. A thin-film forming method according to claim 3, wherein said protective film is a hard carbon film.

5. A thin-film forming method according to claim 1, wherein said thin film forming step utilizes a method selected from the group consisting of a sputtering method, an evaporating method, an ion plating method, a plasma CVD method, an ion-beam sputtering method and an ion implanting method.

6. A thin-film forming method according to claim 1, further comprising the step of scanning said probe in a widthwise direction of said member to be processed, wherein said step of scanning occurs during said step of measuring.

7. A thin-film forming method according to claim 1, further comprising the step of disposing a plurality of probes in a widthwise direction of said member to be processed when the Raman spectrum is measured.

8. A thin-film forming method according to claim 1, further comprising the step of controlling an output of a laser beam from the Raman spectrometer wherein said step of controlling occurs during said step of measuring.

9. A thin-film forming method according to claim 8, wherein said step of controlling an output produces a Raman intensity reflected from the thin film that is substantially constant.

10. A thin-film forming apparatus incorporating a thin-film forming device for forming a thin film on a member to be processed in a vacuum chamber having a reduced pressure, said thin-film forming apparatus comprising:

a measuring device having a probe for measuring a Raman spectrum of a formed thin film and producing a result while said thin film is moving in-line, a focal-point control mechanism for controlling the focal point with respect to the film moving-in line, wherein the apparatus is configured such that the thin-film forming conditions are controlled in accordance with said result.

11. A thin-film forming apparatus according to claim 10, further comprising an elongated-sheet member upon which said thin-film forming device continuously forms said thin film, wherein said measuring device is disposed with respect to said continuously formed thin film in such a manner that said measuring device measures the Raman spectrum.

12. A thin-film forming apparatus according to claim 10, wherein said thin film is a protective film of a magnetic recording medium.

13. A thin-film forming apparatus according to claim 12, wherein said protective film is a hard carbon film.

14. A thin-film forming apparatus according to claim 10, wherein said thin-film forming device forms the thin film by a method selected from the group consisting of a sputtering method, an evaporating method, a plasma CVD method, an ion-beam sputtering method, an ion implanting method and an ion plating method.

15. A thin-film forming apparatus according to claim 10, wherein said measuring device further comprises a laser oscillator and an objective lens.

16. A thin-film forming apparatus according to claim 15, wherein said thin film forming device further comprises a vacuum chamber in which said probe is disposed.

17. A thin-film forming apparatus according to claim 15, wherein said vacuum chamber further comprises a window, and wherein said probe is disposed on the outside of said vacuum chamber of said thin-film forming device at a position opposite to said member to be processed and on which the thin film has been formed through said window.

18. A thin-film forming apparatus according to claim 15, wherein said probe is made to be movable in a widthwise direction of said member to be processed.

19. A thin-film forming apparatus according to claim 15, wherein a plurality of said probes are disposed in a widthwise direction of said member to be processed.

20. A thin-film forming apparatus according to claim 15, wherein said laser oscillator further comprises a control unit for controlling output of a laser beam.

21. A thin-film forming apparatus according to claim 20, wherein a Raman intensity reflected by the thin film is made to be substantially constant by said control unit.

* * * * *